(12) United States Patent
Fink et al.

(10) Patent No.: US 11,737,667 B2
(45) Date of Patent: Aug. 29, 2023

(54) NANOWIRED ULTRA-CAPACITOR BASED POWER SOURCES FOR IMPLANTABLE SENSORS AND DEVICES

(71) Applicant: Arizona Board of Regents on Behalf of the University of Arizona, Tucson, AZ (US)

(72) Inventors: Wolfgang Fink, Montrose, CA (US); Olgierd Palusinski, Tuscon, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 835 days.

(21) Appl. No.: 16/425,054

(22) Filed: May 29, 2019

(65) Prior Publication Data

US 2019/0365225 A1 Dec. 5, 2019

Related U.S. Application Data

(60) Provisional application No. 62/677,584, filed on May 29, 2018.

(51) Int. Cl.
 *A61B 3/16* (2006.01)
(52) U.S. Cl.
 CPC ........ *A61B 3/16* (2013.01); *A61B 2560/0214* (2013.01)
(58) Field of Classification Search
 CPC ............. A61B 3/16; A61B 2560/0214; A61B 5/03–038; A61B 2562/0247; H01G 11/36
 See application file for complete search history.

(56) References Cited

U.S. PATENT DOCUMENTS

| | | | |
|---|---|---|---|
| 7,131,945 B2 * | 11/2006 | Fink | A61B 3/16 600/398 |
| 7,481,534 B2 | 1/2009 | Fink | |
| 7,762,664 B2 | 7/2010 | Fink | |
| 8,078,309 B1 | 12/2011 | Eyre et al. | |
| 8,385,046 B2 | 2/2013 | Palusinski et al. | |
| 2015/0287544 A1 * | 10/2015 | Irazoqui | H01G 11/48 307/104 |

OTHER PUBLICATIONS

Meng, Chuizhou, et al. "Ultrasmall integrated 3D micro-supercapacitors solve energy storage for miniature devices." Advanced Energy Materials 4.7 (2014): 1301269. (Year: 2014).*

* cited by examiner

*Primary Examiner* — Devin B Henson
(74) *Attorney, Agent, or Firm* — Thomas | Horstemeyer, LLP

(57) ABSTRACT

Various examples related to power sources for implantable sensors and/or devices are provided. In one example, a device for implantation in a subject includes circuitry for sensing an observable parameter of the subject and a power source comprising a nanowired ultra-capacitor (NUC), the power source having a volume of 10 mm³ or less. The NUC can have a surface capacitance density in a range from about 25 mF/cm² to about 29 mF/cm² or greater. Such devices can be used for, e.g., ocular diagnostic sensors or other implantable sensors that may be constrained by size limitations.

20 Claims, 11 Drawing Sheets

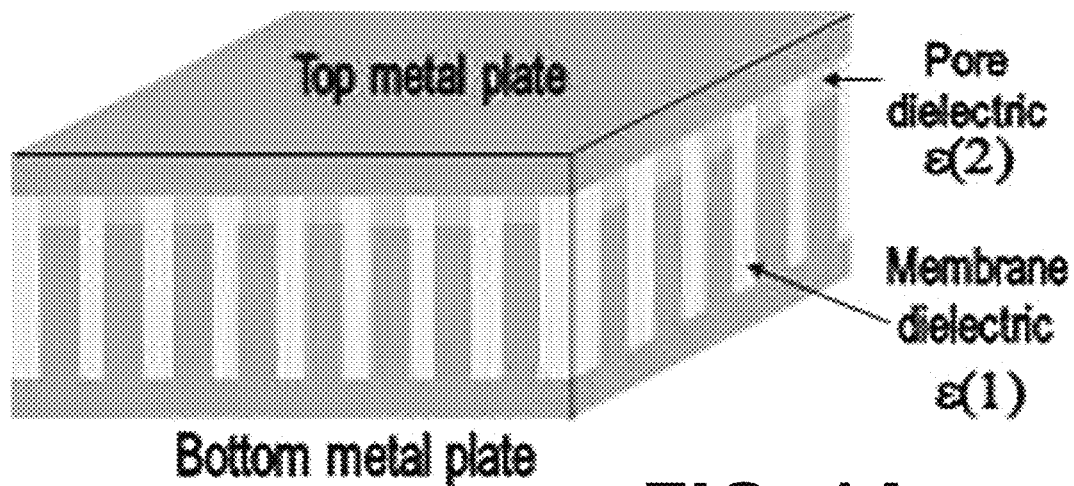
FIG. 1A
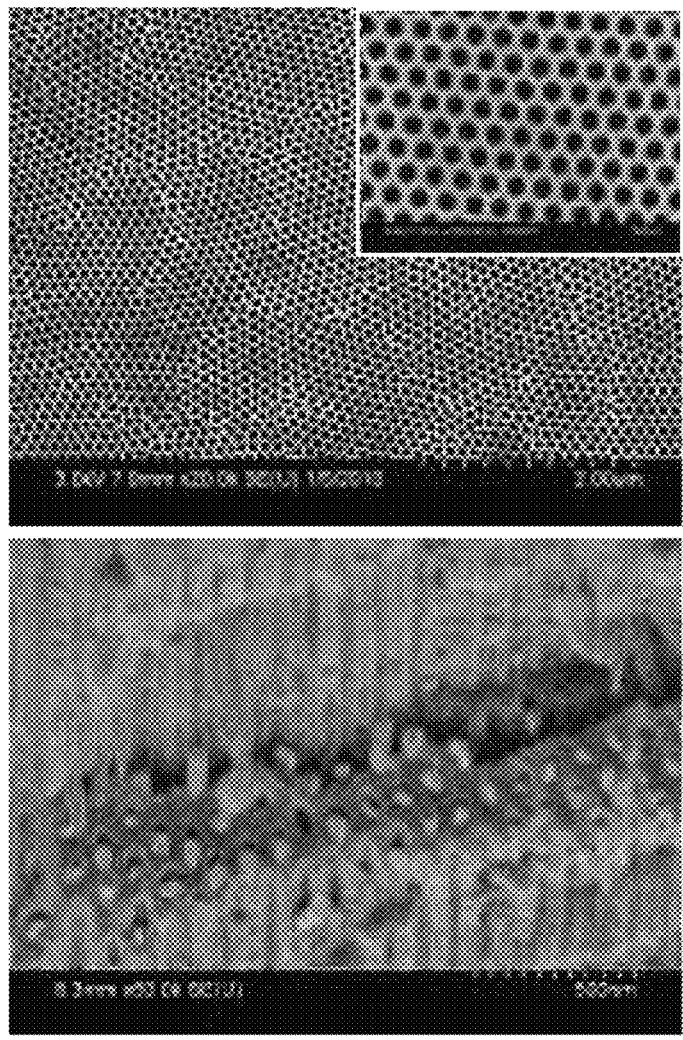
FIG. 1B
FIG. 1C

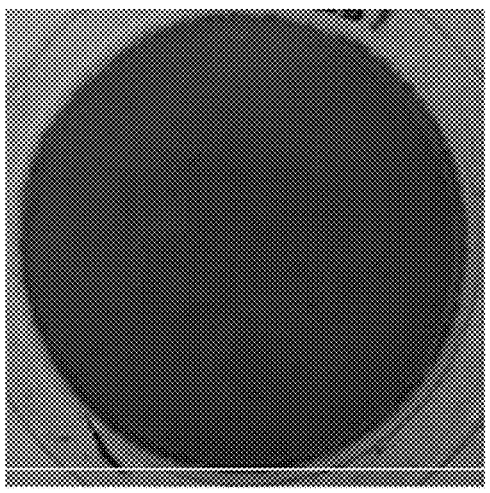
FIG. 3A
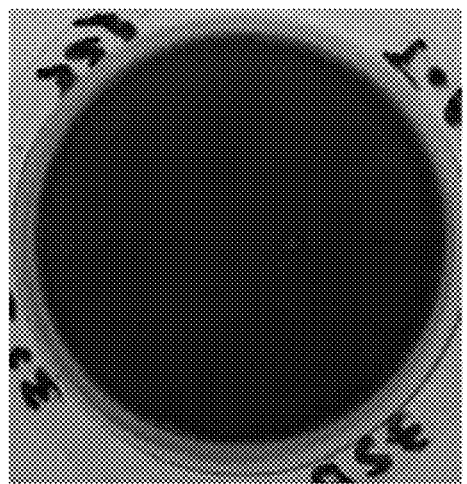
FIG. 3B
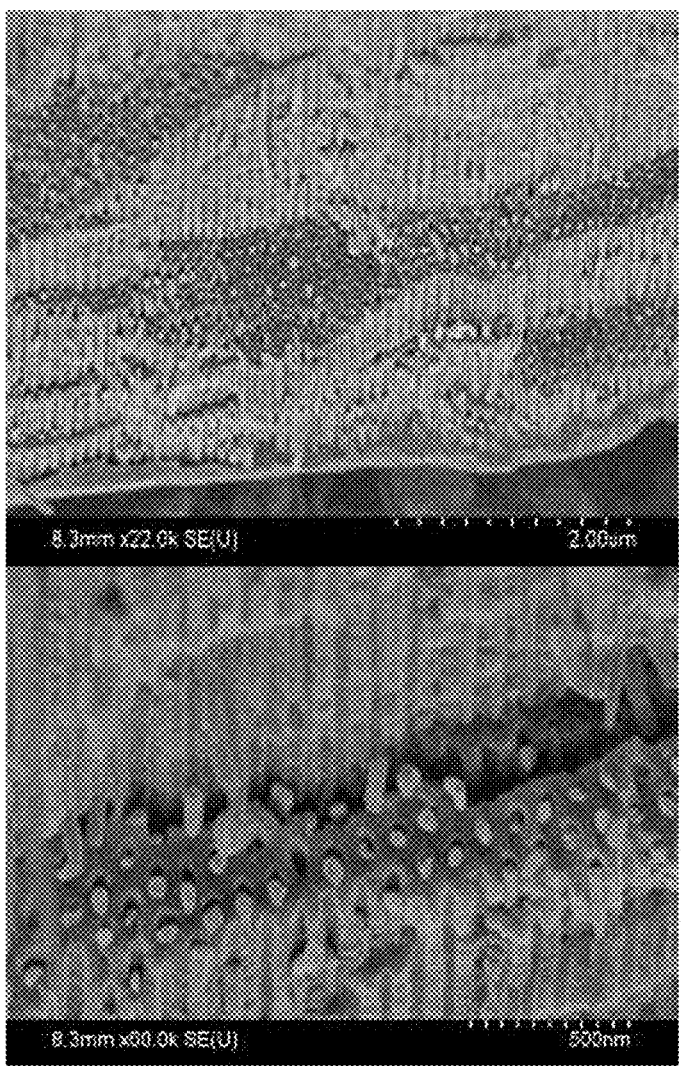
FIG. 4A
FIG. 4B

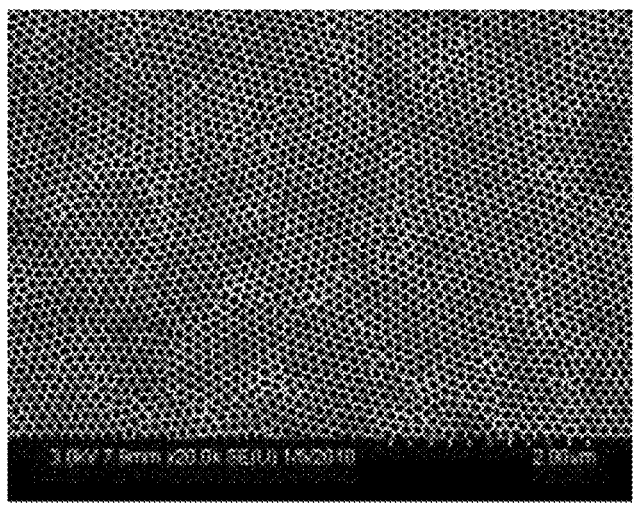
FIG. 7A
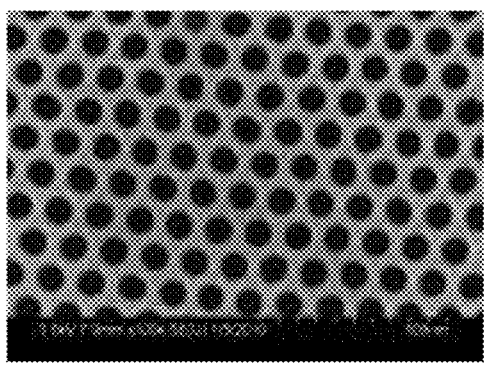
FIG. 7B
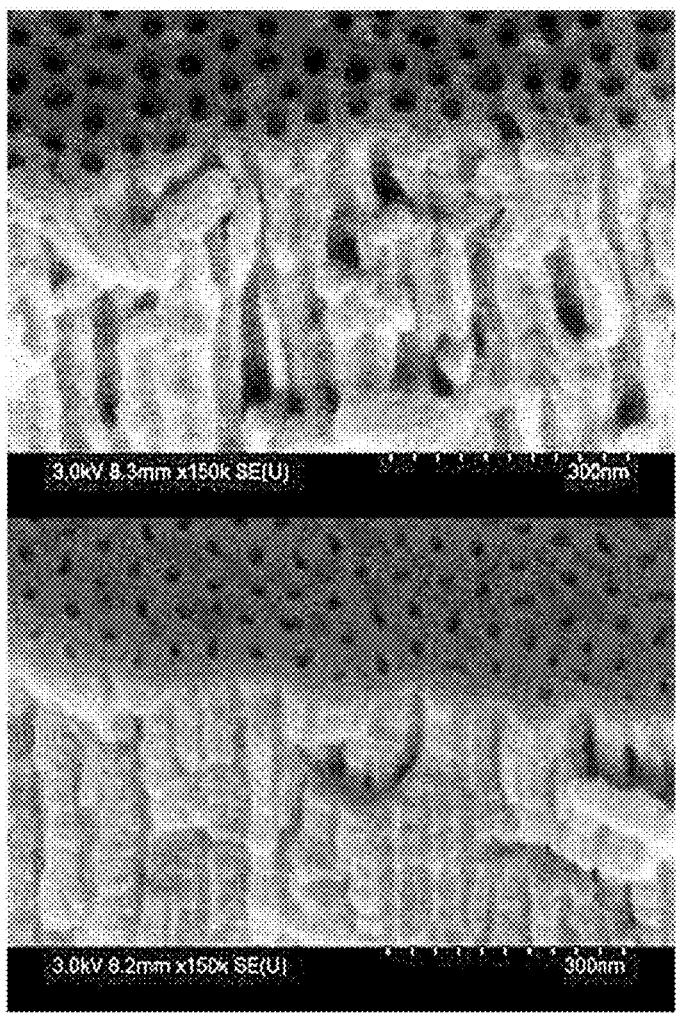
FIG. 8A
FIG. 8B

NANOWIRED ULTRA-CAPACITOR BASED POWER SOURCES FOR IMPLANTABLE SENSORS AND DEVICES

CROSS REFERENCE TO RELATED APPLICATIONS

This application claims priority to, and the benefit of, co-pending U.S. provisional application entitled "Nanowired Ultra-Capacitor Based Power Sources for Implantable Sensors and Devices" having Ser. No. 62/677,584, filed May 29, 2018, which is hereby incorporated by reference in its entirety.

BACKGROUND

Worldwide, the general (elderly) population is increasingly affected by diseases such as major chronic diseases of the eye. Over 285 million people in the world are visually impaired, of whom 39 million are blind and 246 million have moderate to severe visual impairment. It is predicted by the World Health Organization (WHO) that without extra interventions, these numbers will rise to 75 million blind and 200 million visually impaired by the year 2020. According to the WHO, cataract is the leading cause of blindness in the world. However, it is treatable in a straightforward manner through surgery, i.e., replacement of the crystalline lens with an intraocular lens. It is estimated that 67 million people worldwide have glaucoma, up from 60.5 million worldwide in 2010. This number is expected to rise to about 80 million people worldwide by 2020. As such, glaucoma is the 2nd leading cause of blindness in the world. In contrast to cataracts, glaucoma is not curable. At best, the progression of visual field loss due to glaucoma can be stopped or delayed. In light of the above worldwide numbers, early detection of glaucoma and other blinding diseases (e.g., macular degeneration and diabetic retinopathy) is essential as it may allow for actual treatment to avert or at least significantly delay the onset of vision loss.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is a graphical representation of an example of a nanowired ultra-capacitor (NUC), in accordance with various embodiments of the present disclosure.

FIGS. 1B and 10 are scanning electron microscope (SEM) images providing a top view (including enlarged inset image) of an example of a membrane (built in the lab) used in a NUC, and a cross-sectional view of the membrane with copper nanowires, respectively, in accordance with various embodiments of the present disclosure.

FIGS. 3A and 3B are images providing top views of examples of Anodiscs used in a NUC with copper (Cu) plating, in accordance with various embodiments of the present disclosure.

FIGS. 4A-4B and 5A-5B are SEM images providing cross-sectional views of examples of two custom membrane types A and B (built in the lab) electroplated with Cu, in accordance with various embodiments of the present disclosure.

FIGS. 7A and 7B are SEM images providing top views of the first membrane type A of FIGS. 6A-6D showing regular geometry of pores, in accordance with various embodiments of the present disclosure.

FIGS. 8A and 8B are SEM images providing cross-sectional views of an example of the second membrane type B, in accordance with various embodiments of the present disclosure.

FIG. 10 is a schematic diagram illustrating a simple RC circuit used to represent a device under test, in accordance with various embodiments of the present disclosure.

DETAILED DESCRIPTION

Figures 2A, 2B, 2C:
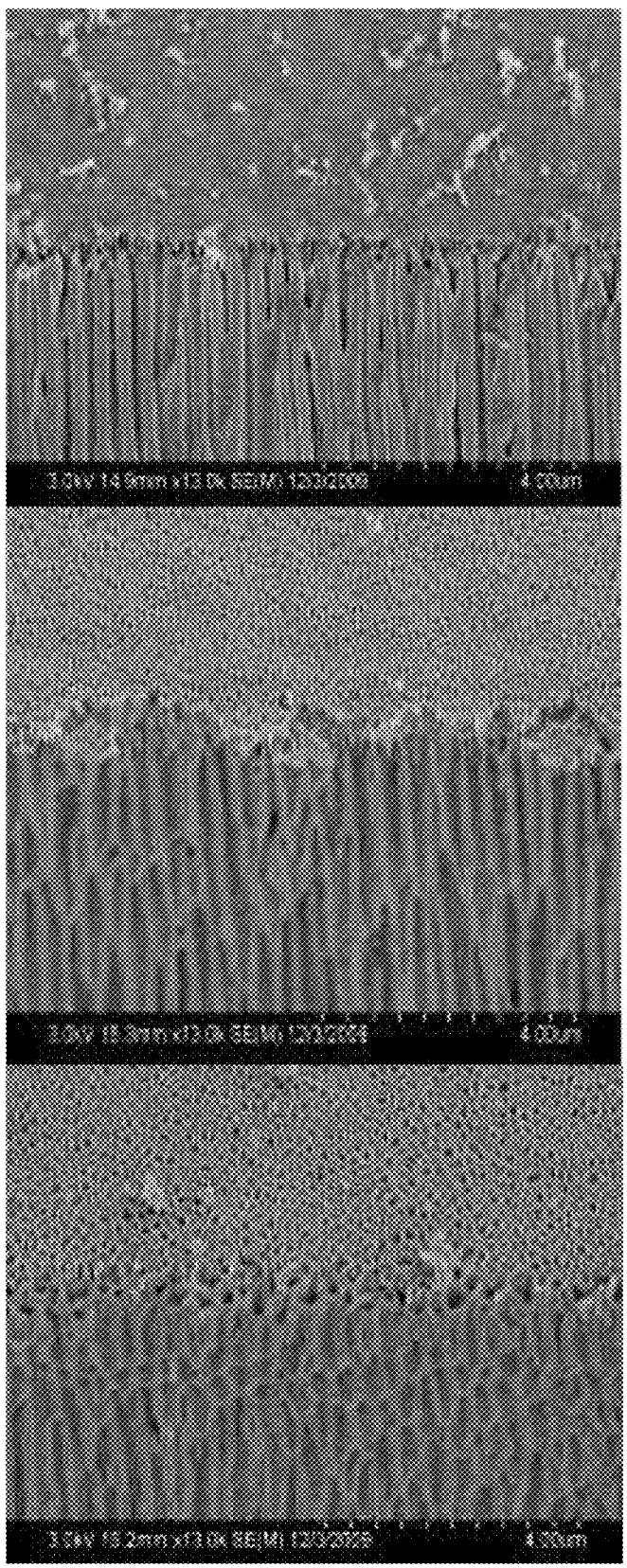
FIGS. 2A-2C are SEM images providing cross-sectional views of examples of commercially available membranes (Anodiscs) with different nominal pore diameters, in accordance with various embodiments of the present disclosure.

Disclosed herein are various examples related to power sources for implantable sensors and/or devices. The power sources can be based on nanowired ultra-capacitor technology. Disclosed herein are various examples related to power sources for sensors and/or devices, implantable in subjects. In one instantiation, a subject can be animate, e.g., one of human, animal, plant, fungus, etc. In yet another instantiation, a subject can be inanimate, such as, but not limited to, an enclosure, a pipe, an engine, a vessel, a pressure vessel, an aircraft wing, etc. Reference will now be made in detail to the description of the embodiments as illustrated in the drawings, wherein like reference numbers indicate like parts throughout the several views.

Implantable sensors and devices can be used in the monitoring and treatment of a variety of diseases. For example, once diagnosed with glaucoma it is important for patients to undergo regular and routine measurements of intraocular pressure (IOP) using tonometers in the doctor's office. The data are used to assess the efficacy of the glaucoma treatment and to direct future course of treatment. However, IOP is variable and may exhibit occasional spikes that may lead to (continued) neural damage while escaping detection in the doctor's office. The result is (further) irreversible visual field loss.

In one instantiation, tonometers are externally applied to the eye (e.g., application of tonometers in direct contact with the cornea, through-the-eye-lid tonometers, airpuff tonometers, etc.), and are not generally customized to take into account individual variations in corneal elasticity. This can lead to significant incidences of false measurements of IOP. In view of this apparent deficiency, e.g., an optically powered and optically data transmitting implantable IOP sensor can be employed (See U.S. Pat. No. 7,131,945, by W. Fink et al., which is hereby incorporated by reference in its entirety). The '945 patent describes one of the first implantable ocular diagnostic devices using an optical rather than radio frequency (RF) communication link between the outside world and an implantable MEMS pressure switch that is coupled to an implantable, optically rechargeable capacitor or battery. The optical output provides an indication of whether a predetermined IOP threshold was exceeded since the last readout. The sensor can provide a record, i.e., memory, of IOP threshold violations, capturing diurnal variations and spikes, which are responsible for the silent progression of glaucomatous visual field loss. It can also provide a reliable patient specific baseline pressure level for ophthalmic healthcare providers to fine-tune the treatment modality for the individual. Other implantable sensor modalities, such as those with a RF communications link or implantable sensors with biophotonic structures or nanostructures, may also be used.

To provide a complete system of systems, associated external opto-mechanical and digital ocular sensor reader systems have been devised and prototyped (See U.S. Pat. Nos. 7,481,534 and 7,762,664, by W. Fink, which are hereby incorporated by reference in their entireties), allowing for eye self-exam and monitoring implants in the anterior ocular chamber, including intraocular pressure sensors. Other external sensor reader systems may also be used.

In order to drive implantable sensors/devices there is a need for biocompatible and ultimately FDA-approved power sources. For example, pacemakers use batteries even though they provide a one-time use power source and need to be replaced periodically. A commonly used power & data transmission mechanism is inductive coupling of external and internal/implanted coil systems. In contrast to this, the use of miniaturized nanowired ultra-capacitors (NUC) to power implantable sensors and/or devices in a battery-like, rechargeable manner is proposed. While the focus here describes the use of NUCs in the context of powering an implantable intraocular pressure sensor, a large multitude of implantable sensors and/or devices for similar or entirely different purposes can be powered by NUCs, without limitation. In addition to implanting sensors/devices in subjects such as humans and animals, sensors/devices can be implanted or incorporated into other subjects such as plants, fungus, or mechanical systems such as enclosures, pipes engines, pressure vessels, etc. For example, sensors can be implanted in mechanical systems or elements for structural health monitoring.

A nanowired ultra-capacitor (NUC) is a high-power-density power source, like a dielectric capacitor with an energy-density that is as high as, or higher than, the state of the art electrochemical supercapacitors and possibly higher than batteries. The combined high power-density and high energy-density embodied in a NUC make it attractive as a replacement or support for many existing power sources (e.g., solar cells or batteries) used to store electrical energy. This is especially true for implantable sensors and/or devices, which are being miniaturized. Advantages of a NUC compared to supercapacitors and batteries include:

Direct storage of electrical energy with high efficiency since no energy conversion is involved in the storing and discharging processes;

Longer life (with high charge and discharge currents) as measured by the number of charge/discharge cycles before degradation (no REDOX chemistry, no chemical wear or decomposition, no toxicity);

Much less of a "memory effect": compared to rechargeable batteries by orders of magnitude, i.e., very little to no wear and tear or degradation as they typically occur in rechargeable batteries during repeated charge and discharge cycles;

Fast charging/discharging (minutes, seconds) with low internal power dissipation in comparison to batteries (hours);

High volumetric and gravimetric energy density with very high power density in device;

Negligible intrinsic self-discharge rate and high self-discharge resistance (batteries and electrochemical supercapacitors have low internal resistance and high self-discharge rates, which requires trickle-charging to maintain their state of charge);

Enhanced ecology and safety, because the NUC is made of non-toxic and non-explosive materials unlike the advanced electrochemical lithium-ion batteries, No problems with overcharging (control circuitry is not needed), which avoids potential of mechanical failure (e.g., explosions);

Possible use of potentially biocompatible materials;

Use of readily-available and inexpensive materials; and

Charging and discharging processes are safe, stable, and without any toxic emissions, offering enhanced safety.

Environmental and safety issues are worth further mention. A NUC can be fabricated using clean low-energy metal anodization and electroplating. There are no toxic materials emitted during the use or disposal of a NUC. These features make the NUC a clean, safe and robust power source. The NUC offers an electrical power source that has high power-density similar to a dielectric capacitor, but can have high energy-density like a battery.

NUCs comprise three thin layers: (i) a thin metal film with a perpendicular array of metal nanowires that can penetrate ¾ of the way into (ii) a thin sheet of porous dielectric membrane and (iii) another thin metal film on the other side of the membrane (See U.S. Pat. No. 8,385,046, by O. Palusinski et al., which is hereby incorporated by reference in its entirety). A NUC can be fabricated using environmentally benign processing. NUC fabrication uses low energy in electroplating, and there are minimal toxic wastes during manufacture. The NUC has minimal thermal gradients due to its nano-dispersed wires and dielectric structure, so a NUC has robust operation even during large and rapid temperature changes. The NUC can be stored for a long time in ambient conditions with no degradation or toxic emission. NUCs can operate over a wide temperature range:

There is nothing to freeze, boil or evaporate;

NUCs can be subjected to rapid temperature cycling without reliability degradation;

Thermal mismatch between membrane and nanowires is minimal, the coefficient of thermal expansion characteristic of the nanowire is close to that of alumina;

NUCs are not sensitive to radiation and thus like glass capacitors can be safely exposed to radiation environments (e.g., CT (Computer Tomography), x-ray, ionizing radiation, etc.); and The use of non-magnetic metals allows the device to be MRI (Magnetic Resonance Imaging) compliant.

A good illustration of a single NUC use is in a "hybrid power-source" in which the NUC can be used to store energy generated by a primary power-source, and can release this energy as high-power pulses when needed. NUCs are useful whenever compact light-weight durable repetitive pulse-power is needed, because a NUC is like a high-energy density dielectric capacitors, which can be quickly and efficiently charged and recharged in any number of series, parallel and series/parallel combinations. This capability makes the NUC a viable power source for implantable sensors and/or devices. The high power-density also makes NUCs suitable for miniaturized applications of such sensors and/or other devices. As such, NUCs offer many benefits for biomedical applications. For example, the NUCs can be collocated with a wide range of sensors and/or devices that are implanted in the body, e.g., above the shoulders. For instance, brain stimulation devices are commonly implanted with leads connecting to a power source that is remotely located on the body. Use of NUCs can significantly reduce the connection length to the power source, which can reduce the physical effects produced by the implanted sensor or device. The use of NUCs with other implantable sensors and/or devices about the head or neck, or other locations where space is limited, offers significant flexibility in the sensor or device placement while also reducing the invasiveness of the implant.

A NUC is an electronic device in that there are no chemical charge transfer reactions and electrical currents are carried only by electrons during the storage of electrical energy and supply of electrical power. This allows for charging on the order of seconds depending on the capacity of the NUC. NUCs can be charged, e.g., through inductive coupling via an implanted coil, or through proper external radiation stimulation of an implanted solar cell (or similar reception device). In one embodiment the external radiation may be polarized. To control the charge of the NUC, the solar cell can be configured to generate energy from a frequency of radiation that is not (or minimally) present in the spectrum of normal daylight. The frequency of the illumination should be able to penetrate the cornea sufficiently to be received by the implanted solar cell. See, e.g., U.S. Pat. No. 7,131,945, which is hereby incorporated by reference in its entirety, for additional discussion of charging that can be applied to a NUC.

As stated above, the NUC comprises metal nanowires in a dielectric medium. As mentioned previously, the NUC is made from clean and safe non-toxic materials, namely, a metal part (like copper, silver, gold, etc.) and a dielectric part (such as polycarbonate, alumina, titania, paraffin, etc.), which makes it suitable for implantation in humans. A NUC supplies higher current and power density than a battery or an electrochemical supercapacitor (ECS). A NUC provides high current because NUC current develops from rapid (microsecond) electronic state changes and it is not due to the slow (milliseconds) reduction-oxidation (REDOX) state changes used in batteries and electrochemical supercapacitors.

Referring to FIG. 1A, shown is a graphical representation of an example of the elements of the NUC technology. As shown, the NUC comprises the array of metal nanowires electroplated in the dielectric membrane connected to a metal layer deposited on one side of the membrane. The metal layer serves as a cathode in the electrodeposition process from which the wires grow in the pores. This metal layer can be called the bottom or lower metal plate or, for short, the bottom electrode. The deposition process can be terminated when the wires reach a certain specified length, which can be controlled by plating parameters, such as deposition time and current density. The length of wires is selected such that pores are only partially filled, for example to ¾ pore length, which is determined by the membrane thickness. Membranes can include, e.g., commercially available Anodiscs (e.g., by Whatman. Ltd) with a thickness of 60 µm. After deposition of the nanowires, the other side of the membrane can be plated with the metal. For short, this metal plate can be called the top or upper electrode. This process creates a dielectric capacitor with one electrode looking like a "bed of nails" formed by the plated nanowires.

Figure 10:
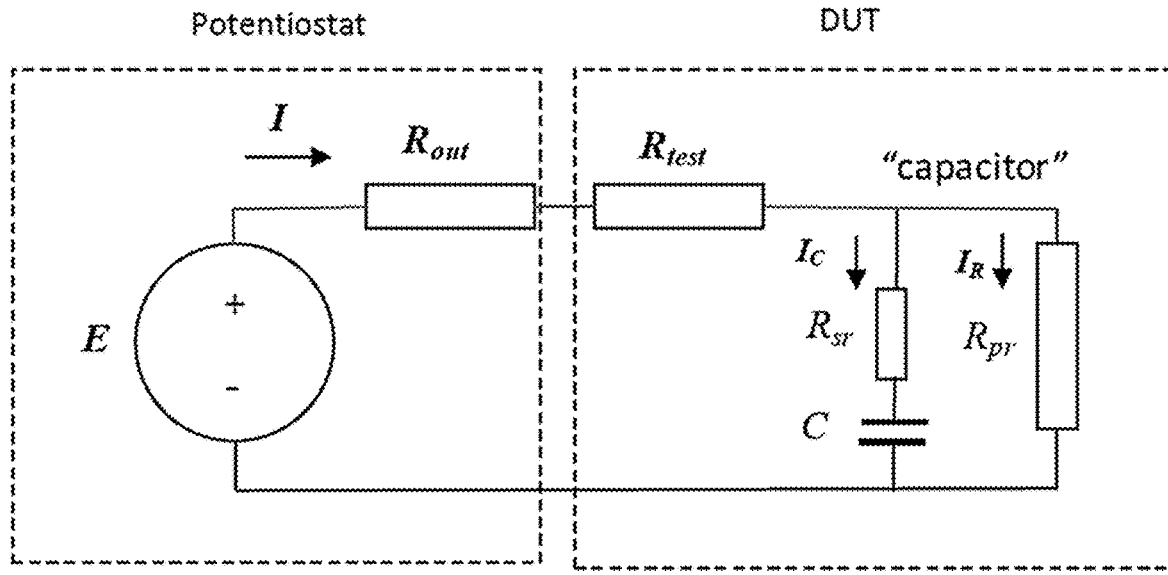

The NUC can be fabricated by electroplating metal wires starting from a metal plate on the bottom side of a dielectric membrane with nanopores. The plating process continues until the metal wire length is about ¾ of the length of the pores. The nanowires are connected in parallel via the bottom plate. A planar metal plate can then be deposited (e.g., by sputtering or vapor deposition) on the topside of the nanoporous membrane. This leaves an air/vacuum gap between the exposed tips of the wires grown from the bottom electrode and the top planar electrode (see the schematic in FIG. 1A). This gap can also be filled by a dielectric material to increase the NUC capacitance. The NUC constructions can use a polycarbonate, alumina ($Al_2O_3$), titania ($TiO_2$) or other suitable membranes. The SEM-image in the FIG. 1B shows an example of a typical alumina membrane fabricated with pores which are around 50 nm in diameter. The inset shows a zoomed-in portion of the membrane. FIG. 10 shows a cross-section of the membrane of FIG. 1B (obtained via breaking the structure) with electroplated copper (Cu) nanowires.

Nanoporous dielectric metal-oxide membranes can be easily and inexpensively fabricated via anodization of metal foil of active metals (such as, aluminum, titanium, zirconium, etc.). A nanoporous metal oxide can be formed on the metal foil by a self-assembly process, in which an electrical bias, applied to the metal in the electrolyte, induces oxidation of the metal to metal ion, which leads to geometrically regular metal pitting yielding hexagonally arranged nanopore formation, followed by formation and precipitation of the metal oxide on the metal. The diameter and density of pores can be controlled by systematically setting parameters of the metal anodization, such as, electrolyte chemistry, temperature, and electrical bias.

A method to create arbitrary sidewall geometries in 3-dimensions using LIGA (lithographie, galvanoformung, abformung) via a Stochastic Optimization Framework has been developed by Eyre and Fink (See U.S. Pat. No. 8,078,309, by F. B. Eyre and W. Fink, which is hereby incorporated by reference in its entirety). The underlying method uses a synchrotron source to expose a PMMA (poly(methyl methacrylate)) substrate through a gold mask for subsequent chemical etching to create a micro-mold. Once the micro-mold is etched, subsequent electroplating yields microstructure-devices. The disclosed method enables microstructures with reentrant angles, which was not previously possible. This method can be applied to the creation of more sophisticated nanowired ultra-capacitor structures, e.g., to enhance electrical capacitance.

NUCs are fabricated by electroplating in nano-porous substrates, which are commercially available, inexpensive, and are also easy and inexpensive to customize. Electroplating has significant manufacturing advantages:

Well known and well controlled process;
Low processing energy;
Low cost of fabrication;
No volatile organic compounds (VOCs) or toxic wastes in manufacturing or disposal; and
Consequently, NUCs are environmentally friendly.

NUC performance can be expressed by its capability to store the electrical energy which is measured by the volumetric and gravimetric energy densities, also called specific energy densities. NUC volumetric or gravimetric energy densities are given in the units of Watt-hour per liter (W·hr/L) or Watt-hour per kilogram (W·hr/kg), respectively. These metrics can be calculated by multiplying the capacitance densities by the half of the square of the maximum operating voltage, which is limited by the dielectric strength of the gap between the top and bottom electrodes and also by properties of any dielectric materials inserted into the gap by the processing. Some fabricated NUCs have been operated with a bias up to 40 V resulting in an energy density of 5 W·hr/kg, which is lower than that of Li-ion batteries, which achieve about 170 W·hr/kg. However, it should be stated that the energy density of a NUC can be improved by further development and optimized processing of the NUC, while energy densities of batteries appear to have already reached the limits.

Factors that can be varied to increase the NUC energy density include:

Voltage—the gap between the nanowires and the upper electrode: 15 μm (about ¼ of the pore length) of alumina would withstand 200 volts resulting in 25 fold density increase yielding 125 W·hr/kg;
New dielectric membrane—the alumina membrane with the relative permittivity of 9.6 can be replaced by the titania membrane with the relative permittivity of 100 thus giving a 10-fold increase of energy density to a level that matches the performance of best known batteries; and/or
Geometry—further design optimization exploiting the geometry of membranes (e.g., pore diameter, density of pores, membrane thickness, the pore fill, etc.) and exploration of different proprietary treatments can yield energy densities exceeding those of batteries.

By integrating these gain factors in the same NUC, the energy density of the NUC power source can exceed that of the best Li-ion batteries. But, a NUC does not have the undesirable battery features, such as: poor cyclability ("memory effect"), low efficiency, low output power, short life time, toxic chemicals and potentially hazardous operation.

Use of Commercial Membranes (Anodiscs).

In the initial work, commercial membranes such as those illustrated in FIGS. 3A and 3B (called Anodiscs and supplied by Whatman, Ltd) were used to build NUCs. There are a few types of Anodiscs distinguished by the pore diameter, d, such as d=20 nm, 40 nm, 100 nm, 200 nm. All of the Anodiscs are 60 μm thick. The availability of Anodiscs with different pore diameters allowed the effect of pore diameter on NUC performance to be exploited. However, experiments revealed that the Anodisc differed by diameter of pores near the one side of membrane going inside a few μm only, which is called the filtration layer. This is because primary application of Anodiscs is filtration. Deep inside all Anodiscs the pore diameters are much much larger and are not related to the nominal diameters; d=20 nm, 40 nm, 100 nm, 200 nm. This is illustrated in FIGS. 2A-2C, which are SEM images of cross-sections of Anodiscs with nominal pore diameters. FIG. 2A shows the pores in the filtration layer (top) and inside the membrane below the filtration layer for a pore diameter of d=20 nm. FIGS. 2B and 2C show similar images for pore diameter of d=100 nm and d=200 nm, respectively. Because of this limitation in Anodiscs, effort was expended to develop and fabricate alumina membranes that are customized for the application. In developing miniaturized sensors and/or devices for implantation, reduction in the size of the NUCs and thus the membranes while maintaining a high energy density and power density becomes important in the customization process.

Anodiscs were used to build NUCs by plating Cu, Ni, and Au. Experiments were used to establish good plating conditions. Examples of the results with plating Cu are shown in the top views of "100 nm" templates in FIGS. 2A (2 hr @−1 mA) and 2B (40 min @−12 mA).

About 2.0 M $CuSO_4$ (no acid)—Max saturation at room temperature;
WE, CE, RE: Cu The Anodiscs with nominal 100 nm diameter pores after plating Cu exhibited uniformity of plating in the pores. Anodiscs were also plated with Au and Ni. Developed plating conditions for Au plating were:

Asymmetric AC plating: $2V_{rms}$ at 60 Hz (Set points: 2.8V vs. Ag/AgCl to −2.8V vs. Ag/AgCl)
Ti—W planar WE
Au CE
Ag/AgCl reference electrode (RE)
2 hr plating time
Electrolyte recipe (0.003 M $HAuCl_4$ (0.93 g/L)/0.5 M $H_3BO_3$ (30 g/L))

Developed plating conditions for Ni plating were:

Const. V @−1V vs. Ag/AgCl
Watts Nickel Plating Bath (8.4 M $NiSO_4$, 2.3 M $NiCl_2$, 6 M $H_3BO_3$)
Ti—W planar WE
Ni CE
Ag/AgCl RE
10 min plating The NUCs with Au nanowires and Ni nanowires were fabricated and characterized. The NUCs with nanowires formed by plating Ni showed higher capacitance density when treated with one ionic liquid (IL). There are many ionic liquids. Use of an IL may be limited by its lack of biocompatibility. It should be noted that further studies in the usefulness of ILs in NUCs should be carried out to determine its stability in time, temperature, voltage and resistivity. Resistivity determines the NUC self-discharge, which is an important feature of the device.

Use of Custom Membranes.

Figures 5A, 5B:
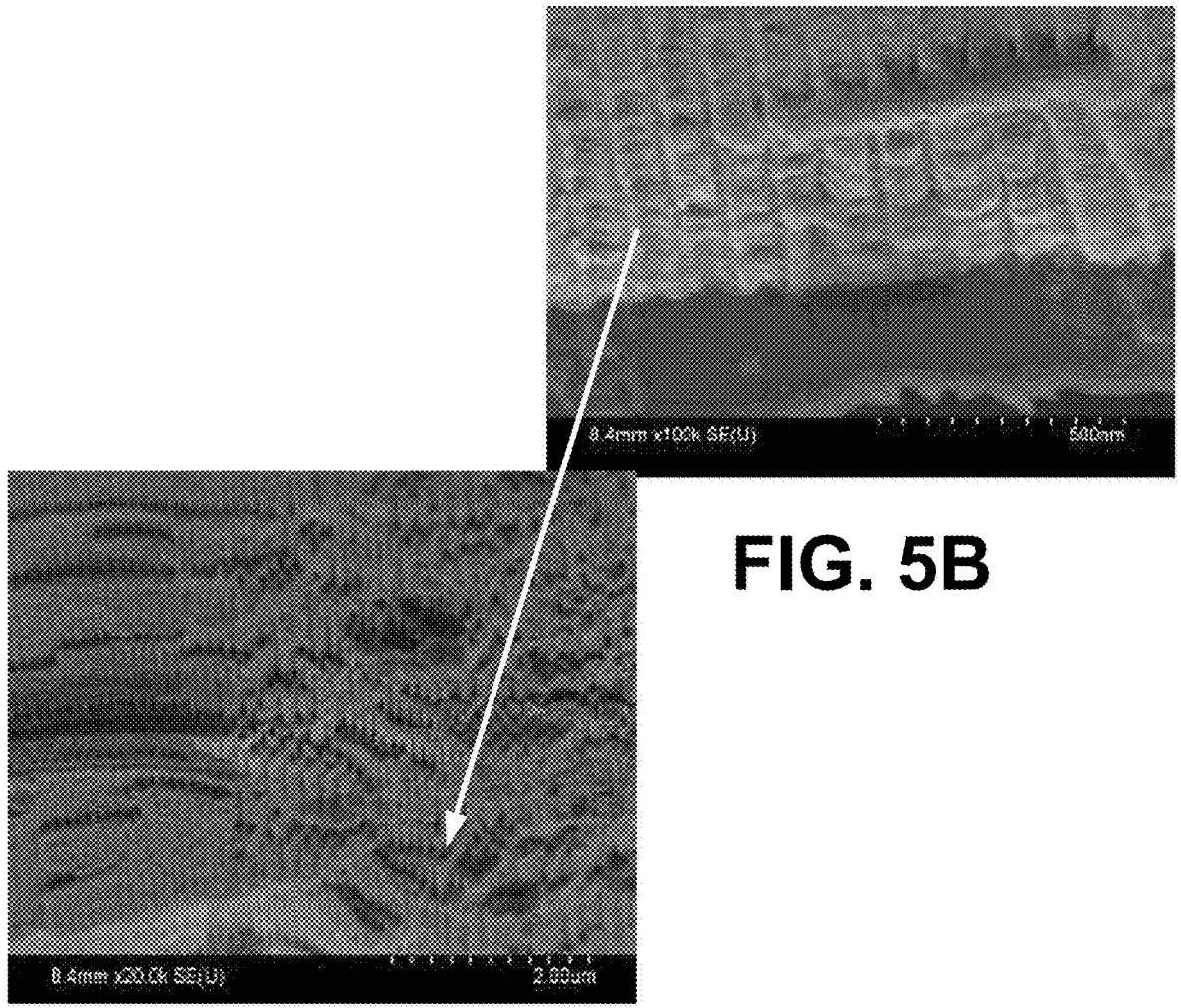

Custom membranes were fabricated via anodization of high-quality (99.99% purity) aluminum foils. Three types of custom membranes were prepared: a first membrane type A which is 65 μm thick and has pores of diameter (50-60) nm as illustrated in FIGS. 4A and 4B, a second membrane type B which is 45 μm thick and has pores of diameter (20-30) nm as illustrated in FIGS. 5A and 5B, and another membrane type D which is 70 μm thick and has pores of diameter (125-225) nm. The pore diameters vary with anodization conditions, but in contrast to Anodisc membranes the geometry of pores in the custom membranes is quite uniform. Details of fabrication and sample SEM images are discussed below. The membrane types A and B were successfully plated with Cu. Because of time constraint only the NUCs built using the membranes A and B were fully tested. Development of technology for fabrication of membrane type D was more challenging because the process required higher voltages (about 200 volts) in the anodization and thus generated more heat such that very efficient cooling was needed. Consequently, the membranes of type D were fabricated at the end of the project and there was not enough time to build a NUC using type D membranes. Type D membranes may be useful in fabrication of solar cells or other applications using silicon plating technology. This technology can be especially attractive for building hybrid sustainable power sources like solar cells with parallel NUC type charge storage all implemented in a monolithic structure.

Membranes type A and B were electroplated with Cu. FIGS. 4A-4B and 5A-5B illustrate results of plating Cu in the membranes type A and B. The plating conditions for the membrane type A with a diameter of pores about 50 nm were: constant current density 1 mA/cm$^2$ for 4 hours, with the electrolyte 1 M CuSO$_4$.5H$_2$O+H$_2$SO. Copper in the membrane of type A appears to be plated adequately and uniformly. FIG. 4A is a SEM image of the cross-section of membrane type A electroplated with Cu, where the cross-section was obtained by breaking the structure, and FIG. 4B is an enlargement of a small segment of this cross-section. The plating conditions for the membrane type B with a diameter of pores about 20 nm were: constant current density 1 mA/cm$^2$ for 4 hours and the electrolyte 1 M CuSO$_4$.5H$_2$O+H$_2$SO$_4$. Copper seems to be inadequately plated such that Cu is missing in some pores. FIG. 5A is a SEM image of the cross-section of membrane type B obtained by breaking the structure. FIG. 5B is an enlargement of a small segment at the bottom of the membrane cross-section. As can be seen, the pores in this very small section are not filled, Cu is not visible. It is possible that the electrolyte could not penetrate some pores. However, additional work could obtain satisfactory plating.

Fabricated Membrane Type A.

Figure 6B:
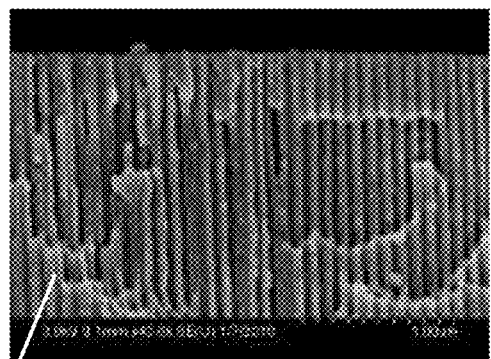
FIGS. 6A-6D are SEM images providing cross-sectional views of an example of the first membrane type A showing regular geometry of pores, in accordance with various embodiments of the present disclosure.
Figure 6A:
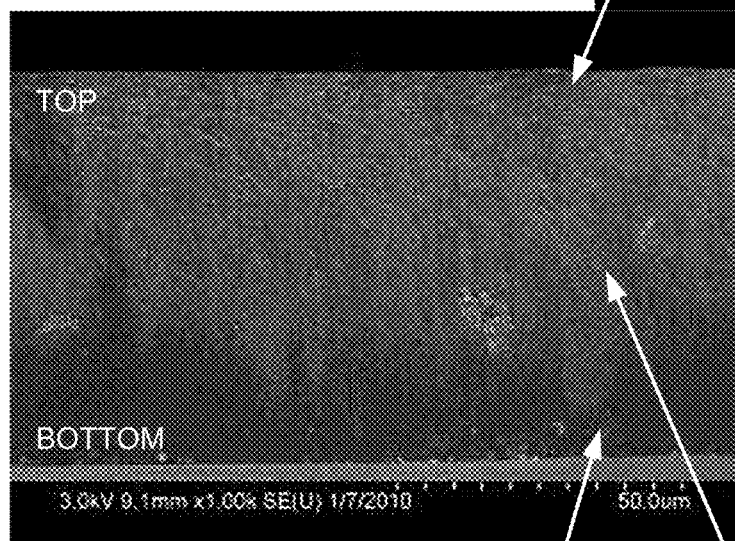
Figure 6D:
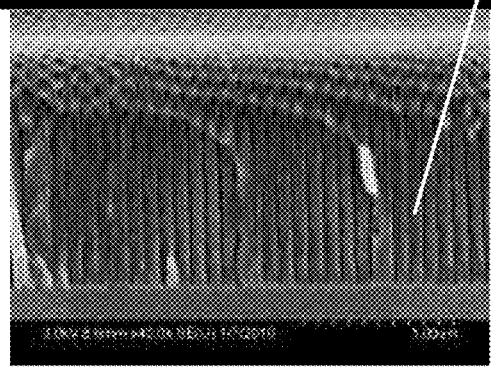
Figure 6C:
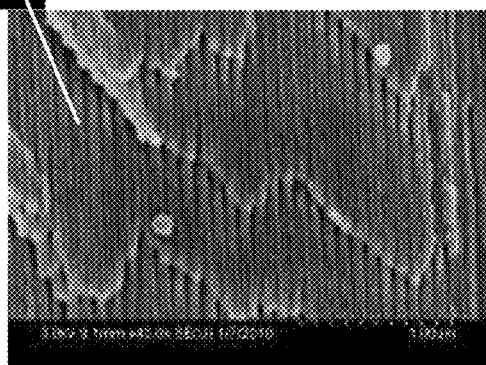

SEM images of the fabricated membrane type A is shown in FIGS. 6A-6D and 7A-7B. FIG. 6A is a SEM image of a cross-section view of the membrane type A with enlarged images of the top, middle and bottom areas shown in FIGS. 6B, 6C and 6D, respectively. FIG. 7A is an SEM image of the bottom of the membrane type A with a zoomed in area shown in FIG. 7B to illustrate the uniformity of the pores.

Fabricated Membrane Type B.

SEM images of the fabricated membrane type B fragments are shown in FIGS. 8A and 8B. FIG. 8A is an image at the top of the fragment of the membrane type B showing fairly regular pores, and FIG. 8B is an image at the bottom of the fragment, where the pores are less uniform.

Fabricated Membrane Type D.

Figure 9A:
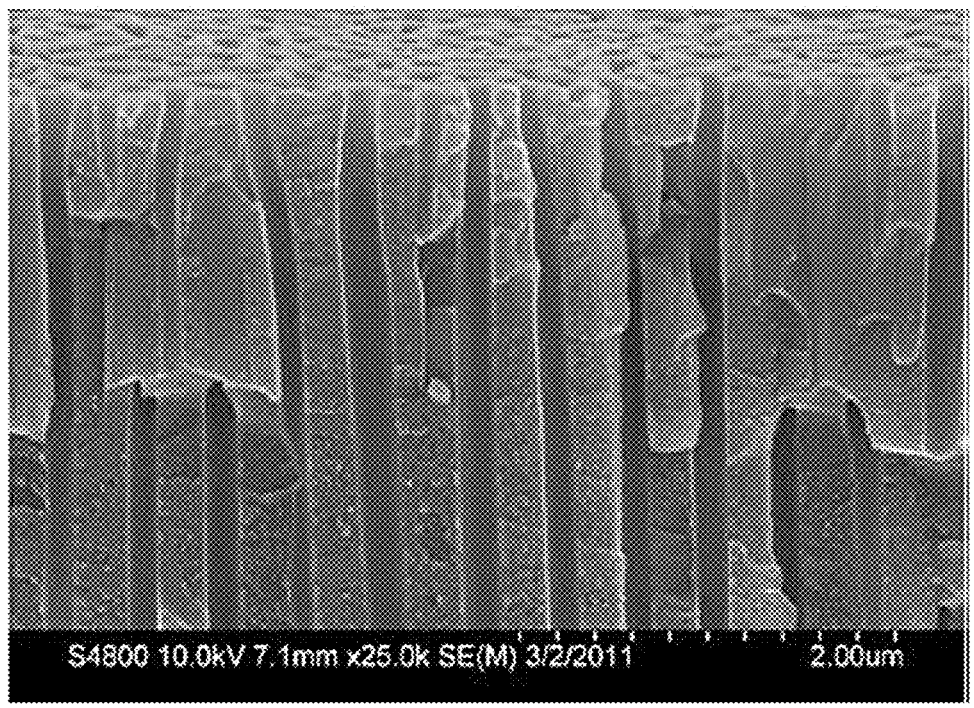
FIGS. 9A and 9B are SEM images providing cross-sectional views of examples of another membrane type D in accordance with various embodiments of the present disclosure.
Figure 9B:
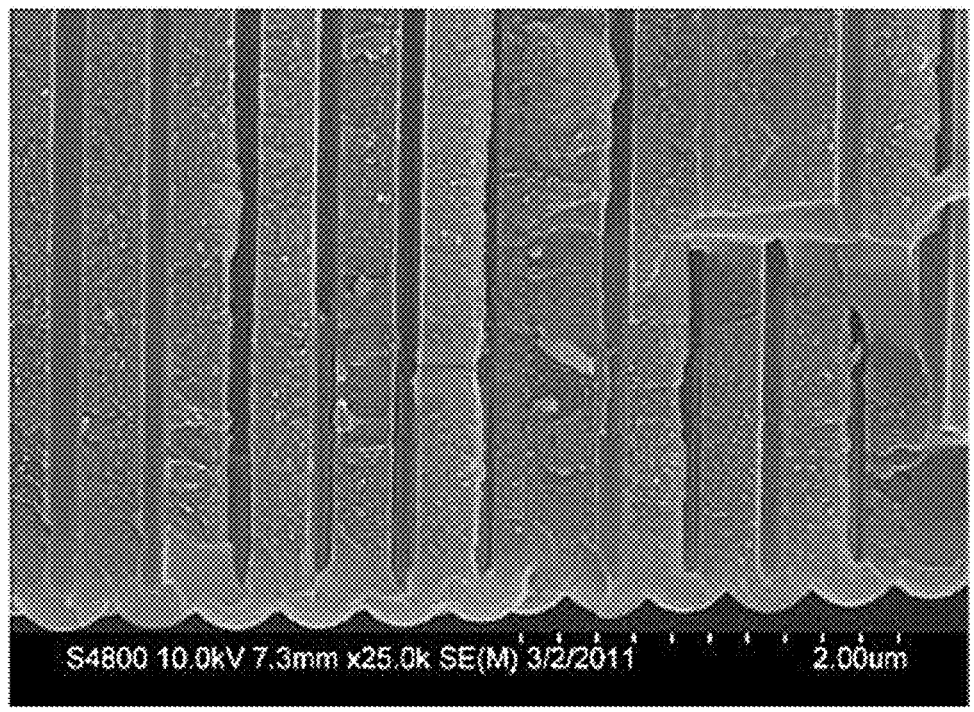

Two examples of the fabricated membrane type D are given to illustrate the work accomplished. FIG. 9A is an SEM image near the top of a membrane type D cross-section, with a pore diameter of 150 nm and pore pitch of 470 nm. FIG. 9B is an SEM image near the bottom of a membrane type D cross-section, with a pore diameter of 125 nm and pore pitch of 440 nm. The barrier layer is visible.

Characterization by Cyclic Voltammetry.

In the cyclic voltammetry (CV), the potentiostat voltage source, E, is swept cyclically and linearly in time, t, between two voltage levels: $E_L$ and $E_R$ such that $E=E_o \pm kt$, where k designates the sweep rate. Often the sweep is "symmetric" (i.e., the voltage is swept between $-E_{mx}$ and $E_{mx}$). To simplify discussion, a simple RC circuit is shown in FIG. 10 is used to represent the device under test (DUT) and "symmetric" sweep is assumed. Further simplification in the analysis is that the external resistor, $R_{test}$, sometimes added in testing is omitted i.e. $R_{test}=0$.

The DUT in FIG. 10 is represented by the effective capacitor, C, the equivalent series resistor, $R_{sr}$, and the equivalent parallel resistor, $R_{pr}$ (the self-discharge resistor). These three parameters together with the maximum operating voltage, device volume and weight are sufficient to determine the performance of the storage device ("capacitor"), such as energy density, power density, energy efficiency, self-discharge, time to charge. The three parameters (C, $R_{ST}$, $R_{pr}$) are unknown, to be determined using CV processing and resulting I-V plot. An example of a plot showing the trajectory generated with the sweep rate of k=0.1 V/sec using the potentiostat running CV with the NUC fabricated in Anodisc is shown in the FIG. 11.

Figure 11:
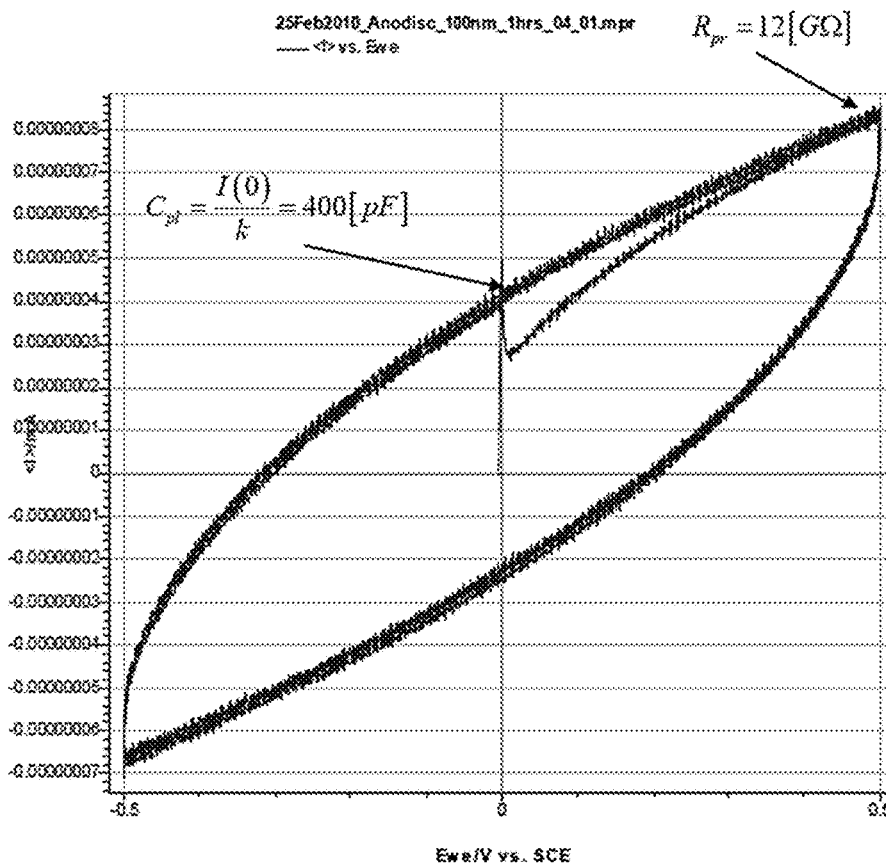
FIG. 11 is a plot of illustrating an example of a trajectory generated using cyclic voltammetry (CV) applied to a NUC fabricated with a commercial membrane, in accordance with various embodiments of the present disclosure.

The capacitance is routinely determined using the formula $C_{pl}=I(0)/k$, where I(0) is the current read when the trajectory crosses the voltage axis, i.e., when E=0. The subscript pl is used here to indicate that the capacitance is determined from the plot and it is only an approximation (see discussion to follow). The self-discharge resistor is determined by the slope of the trajectory:

$$\frac{dI(E_{mx})}{dE} = \frac{1}{R_{pr}}, \qquad (1)$$

when the trajectory reaches steady state at $E=E_{mx}$. The readings are shown in the plot of FIG. 11. The trajectory in forward sweep (k>0) in the equivalent circuit of FIG. 10 is:

$$I(E) = \frac{E}{R_{pr}} + kC\left[1 - \frac{2e^{-(E_{mx}+E)/kT}}{1 + e^{-2E_{mx}/kT}}\right]; T = [R_{out} + R_{sr}]C. \qquad (2)$$

The current when the trajectory crosses the current axis is:

$$I(0) = kC\left[1 - \frac{2e^{-E_{mx}/kT}}{1 + e^{-2E_{mx}/kT}}\right]. \qquad (3)$$

Thus, the capacitance is:

$$C = \frac{I(0)}{k} \frac{1 + e^{-2E_{mx}/kT}}{(1 - e^{-E_{mx}/kT})^2}. \qquad (4)$$

This shows that the capacitance reading should be multiplied by the correcting factor:

$$\xi_{cor} = \frac{1 + e^{-2E_{mx}/kT}}{(1 - e^{-E_{mx}/kT})^2}. \qquad (5)$$

The accuracy of reading ($C_{pl}$) increases exponentially with the factor $E_{mx}/kT$, which indicates that low sweep rates and high voltage swings improve the accuracy. It should be noted here that the time constant T is unknown. An easy way to check accuracy of capacitance reading is to run a series of CV experiments with decreasing sweep rates.

Figure 12:
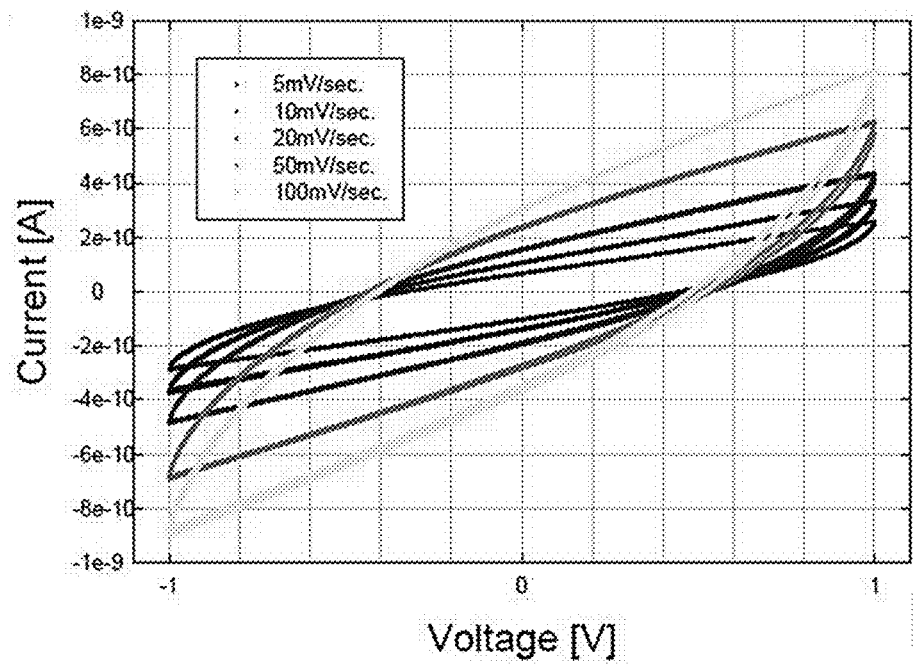
FIG. 12 is a plot illustrating an example of current-voltage trajectory generated using CV applied to the fabricated NUC, in accordance with various embodiments of the present disclosure.

An example of such an experiment with the NUC fabricated in the membrane type A is shown in FIG. 12, which shows current-voltage trajectories generated via CV for the NUC fabricated with membrane type A. The plating conditions were 1 M $CuSO_4.5H_2O+0.2$ M $H_2SO_4$; 2 $mA/cm^2$ for 1 hr, and the area of the top electrode was 0.24 $cm^2$. The plots correspond to the series of decreasing sweep rates (100 mV/sec, 50 mV/sec, 20 mV/sec, 10 mV/sec, 5 mV/sec), and capacitance readings increase with the decreasing rates with the values appearing to converge (3 nF, 4.78 nF, 7.7 nF, 10.8 nF, 13.2 nF). The trajectory equation (2) can be used to determine the slope at the extreme potential:

$$\frac{dI(E_{mx})}{dE} = \frac{1}{R_{pr}} + \frac{2}{R_{out}+R_{sr}} \frac{e^{-2E_{mx}/kT}}{1+e^{-2E_{max}/kT}}, \quad (6)$$

which shows that the correct expression for the self-discharge resistor, $R_{pr}$, is:

$$\frac{1}{R_{pr}} = \frac{dI(E_{mx})}{dE} - \frac{2}{R_{out}+R_{sr}} \frac{e^{-2E_{mx}/kT}}{1+e^{-2E_{mx}/kT}}, \quad (7)$$

and its accuracy can be improved by increasing the ratio $E_{mx}/k$.

The time constant $T=[R_{out}+R_{sr}]C$ present in the above formulas is unknown because it depends on an unknown equivalent series resistance, $R_{sr}$. The value $R_{out}$ should be given by the manufacturer of the potentiostat or may be easily measured loading the potentiostat with known resistor. Typically $R_{out}$ is very small on the order of a fraction of Ohm. Considering equation (3), the unknown time constant and the equivalent series resistor can be determined in the following procedure. It is convenient to introduce the notation for the unknown in the form $x=e^{1/T}$, for the quantity (approximate capacitance) read from the plot $C_{pl}=I(0)/k$ and for the quantity determined by the potentiostat setting $\alpha=E_{mx}/k$. This notation used in equation (3) yields:

$$C = C_{pl} \frac{1+x^{\alpha}}{(1-x^{\alpha})^2}. \quad (8)$$

Two different settings of potentiostat denoted by $\alpha_1$ and $\alpha_2$ result in two different reading from the plot $C_{pl1}$ and $C_{pl2}$ and equation (8) yield:

$$C = C_{pl1} \frac{1+x^{\alpha_1}}{(1-x^{\alpha_1})^2} \text{ and } C = C_{pl2} \frac{1+x^{\alpha_2}}{(1-x^{\alpha_2})^2}. \quad (9)$$

The equations (9) involve two unknowns: C and x. Elimination of C yields the equation for the unknown, x, in the form:

$$C_{pl1} \frac{1+x^{\alpha_1}}{(1-x^{\alpha_1})^2} = C_{pl2} \frac{1+x^{\alpha_2}}{(1-x^{\alpha_2})^2}. \quad (10)$$

A numerical solution yields, x, which yields $T=\ln(1/x)$, and C from one of the equations (9). Finally the equivalent series resistance can be calculated from $T=C(R_{out}+R_{sr})$.

Characterization of Charge-Discharge Processes.

Charge/discharge processes are also called coulometry techniques (denoted here by the abbreviation CM). In the CM measurement, the potentiostat can be programmed to periodically charge the tested NUC at a constant voltage, E, applied for a specific duration of time and after that discharge (e.g., set the voltage to zero for another interval of time). The potentiostat stores the charging and discharging currents for the prescribed number of intervals. The NUC capacitance can be calculated using integrals of the currents as explained below. During the CM, the NUC is powered by a series of rectangular voltage pulses. The initial charging current is very large and drops rapidly over time because the charge collection in the NUC creates increasing counter potential. This rapid variation of the current is difficult to capture because of instrument limitations and finite time required for analog to digital conversion of the directly measured analog values of the current. Because of these limitations the NUC is typically put in series with a large resistor, $R_m$ (~$M\Omega$) to limit the current and slow the current decay rate. Another option to deal with the instrument limitations is to program the instrument to generate pulses of trapezoidal shape with controlled ramping. Here, rectangular pulses were used in all experiments because the calculation of capacitance is much simpler.

Figure 13A:
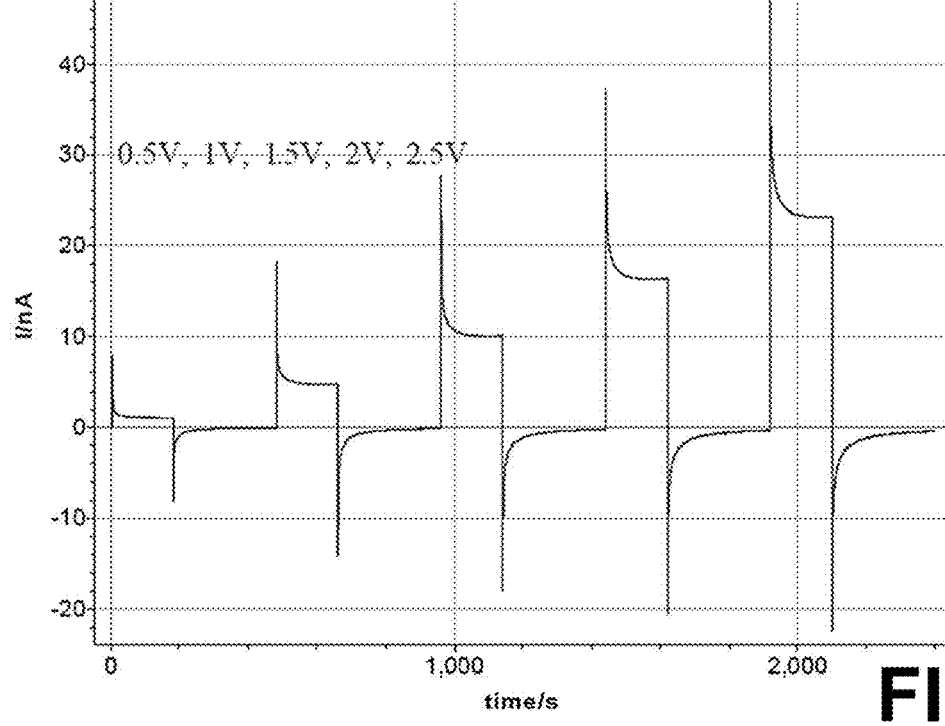
FIGS. 13A and 13B are plots illustrating examples of charge-discharge currents in the CV measurements of the fabricated NUC, in accordance with various embodiments of the present disclosure.
Figure 13B:
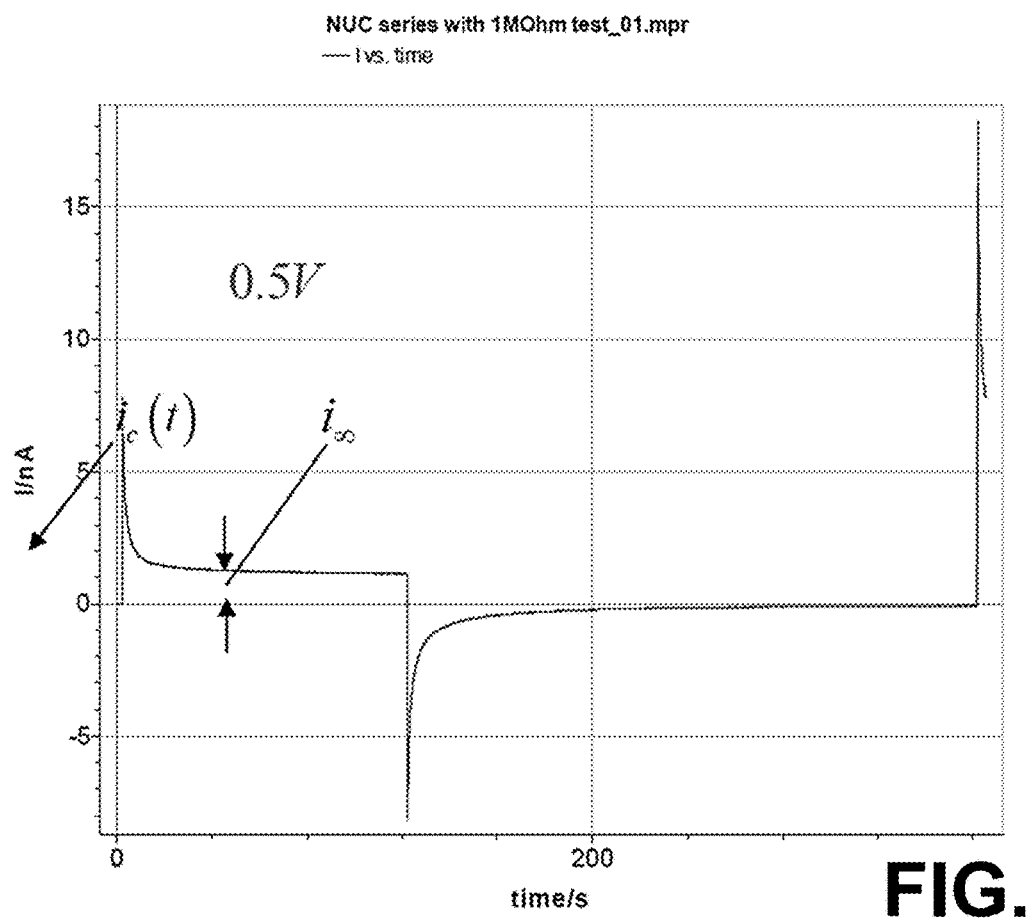

FIG. 13A shows a plot of charge discharge currents in the CM measurements with the NUC in series with a 1 $M\Omega$ resistor. The applied voltages in the series are 0.5V, 1V, 1.5V, 2V and 2.5V. The potentiostat can be also programmed to change the applied rectangular voltage pulse from interval to interval as shown in FIG. 13A. FIG. 13B shows a zoomed in view of one charge discharge cycle to illustrate the calculation of the NUC capacitance. The applied voltage is E=0.5V with a series resistor of $R_m$=1 $M\Omega$. The charging current is designated by the symbol $i_c(t)$ and the symbol $i_\infty$ designates the leakage current. The charge stored in the NUC integrated for a sufficiently long time, until the current reaches the constant level (leakage current) is:

$$Q_m = \int_0^t [i(\tau) - i_\infty] d\tau. \quad (11)$$

The capacitance can be approximately calculated using the formula:

$$C = Q_m/E. \quad (12)$$

The commonly used formula of equation (12) should be corrected when the leakage current, $i_\infty$, is large enough such that the voltage drop on the series resistance, $R_m i_\infty$, is not negligible with respect to the applied voltage. In such a case the correct formula is given by:

$$C = \frac{Q_m}{E - i_\infty R_m}. \quad (13)$$

In the example given here ($R_m$=1 $M\Omega$, $i_\infty$=2 nA) the voltage drop is $i_\infty R_m = 2 \cdot 10^{-3}$V and can be considered negligible with the applied voltage E=0.5V. The leakage current can also be used to determine the equivalent self-discharge resistor, $R_{pr}$, using the formula $R_{pr}=E/i_\infty$, which in the case of the tested NUC yields $R_{pr}$=250 $M\Omega$.

Characterization Via Measurements of Electrochemical Impedance Spectrum (EIS).

Basic features of EIS include:

"small signal" analysis—non-linear effects are not accounted for;

uses sinusoidal excitations of NUC;
calculation of real (Re(ω)) and imaginary (Im(ω)) components of impedance using orthogonality of Fourier series—nonlinear effects are not included;
calculation of impedance magnitude and its logarithm for a series of frequencies:

$$\log\{|z(\omega)|\}=\log\{\sqrt{[Re(\omega)]^2+[Im(\omega)]^2}\}; \omega=2\pi f \text{ } f\text{-frequency }[Hz];$$

and
calculation of phase:

$$\varphi(\omega) = \arctan\frac{Im(\omega)}{Re(\omega)}.$$

Figure 14:
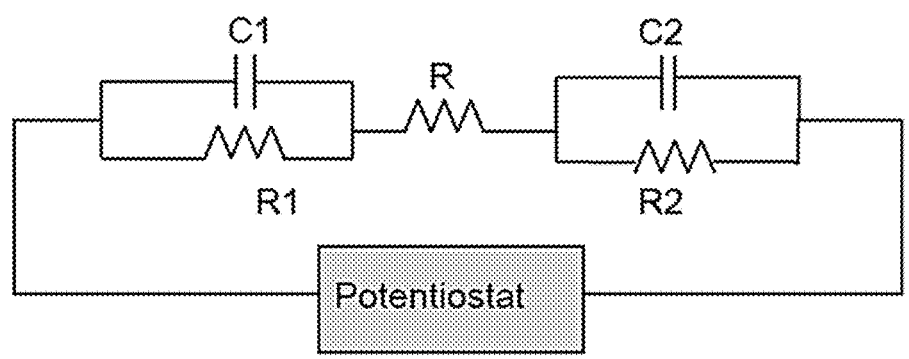
FIG. 14 is a schematic diagram illustrating an example of a circuit used in an electrochemical impedance spectrum (EIS) procedure, in accordance with various embodiments of the present disclosure.

Referring to FIG. 14, shown is a schematic diagram illustrating an example of a circuit to illustrate the EIS procedures. In the steady DC state, the capacitors (C1 and C2) of FIG. 14 do not conduct and are charged to $Q_1=iR_1C_1$ and $Q_2=iR_2C_2$. The current, i, flowing through the resistors is:

$$i = \frac{E}{R_1 + R + R_2}.$$

The effective ("global") capacitance, $C_{eff}$, is defined by $Q=C_{eff}E$, where $Q=Q_1+Q_2$ is the charge stored in the network, or:

$$C_{eff} = \frac{Q}{E} = C_1\frac{R_1}{R_1 + R + R_2} + C_2\frac{R_2}{R_1 + R + R_2}.$$

To compute the effective capacitance one has to know the network topology and compute the values of its components. The impedance of the measured circuit showing the real and imaginary parts can be given by:

$$Z = R + \frac{R_1}{1 + (\omega T_1)^2} + \frac{R_2}{1 + (\omega T_2)^2} - j\omega\left[\frac{R_1 T_1}{1 + (\omega T_1)^2} + \frac{R_2 T_2}{1 + (\omega T_2)^2}\right],$$

with $T_1=C_1R_1$, $T_2=C_2R_2$. Given the measured data:

$$\log\{|z_m(\omega)|\}=F_{meas}(\omega) \text{ and } \varphi_{meas}(\omega),$$

and the calculated ones (with circuit topology assumed):

$$\log\{|z_c(\omega)|\}=F_{calc}(\omega) \text{ and } \varphi_{calc}(\omega),$$

error metrics can be defined using a specific mathematical norm as follows:

$$\epsilon_F \|F_{meas}(\omega)-F_{calc}(\omega)\|; \epsilon_\kappa=\|\varphi_{meas}(\omega)-\varphi_{calc}(\omega)\|.$$

These metrics are minimized with respect to the circuit parameter values using, e.g., numerical optimization. Illustration of a specific metric for the circuit of FIG. 14 is given by:

$$\epsilon_F = \min \int_{\omega_{min}}^{\omega_{max}} \left| F_{meas}(\omega) - \log\sqrt{\left[R + \frac{R_1}{1 + (\omega T_1)^2} + \frac{R_2}{1 + (\omega T_2)^2}\right]^2 + \left[\frac{\omega R_1 T_1}{1 + (\omega T_1)^2} + \frac{\omega R_2 T_2}{1 + (\omega T_2)^2}\right]^2} \right| d\omega,$$

where the minimization is with respect to $R_1$, $R_2$, $C_1$ and $C_2$. Thus, the EIS procedure includes: (a) computation of impedance (small signal); (b) selection of device equivalent network; (c) computation of values of network components (optimization); and (d) calculation of effective capacitance via network analysis with computed component values (does not capture nonlinear effects).

Sensors and/or Devices for Implantation.

Figure 15A:
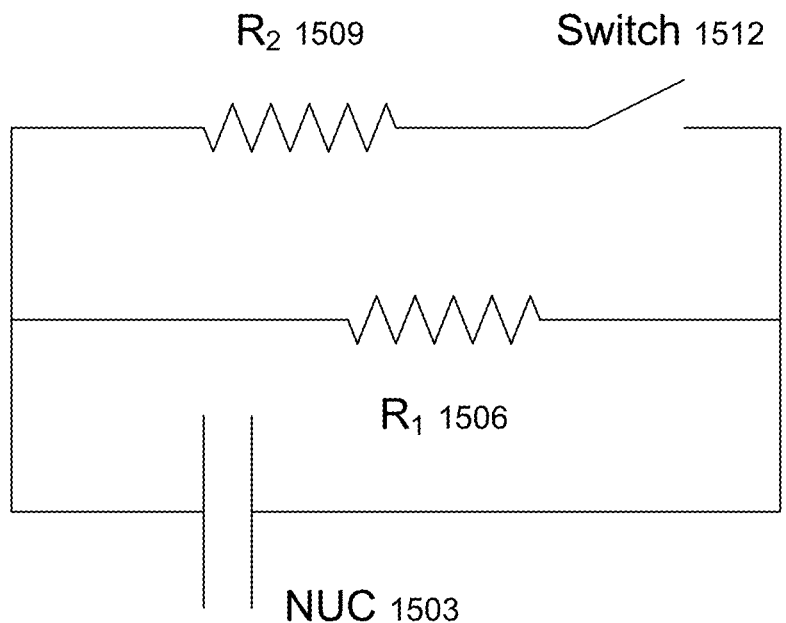
FIGS. 15A and 15B show a schematic diagram illustrating an example of an implantable sensor for monitoring intraocular pressure (IOP) and an example of a NUC discharge curve, respectively, in accordance with various embodiments of the present disclosure.

The following disclosure describes in more detail the specifications and charge, storage, and discharge characteristics of NUCs in the context of powering an implantable intraocular pressure (IOP) sensor as one instantiation. Referring to FIG. 15A, shown is a schematic diagram illustrating an example of an implantable IOP sensor circuit including a NUC 1503 and a discharge resistance $R_1$ 1506. The implantable IOP sensor also includes a sensing discharge resistor $R_2$ 1509 in series with a microswitch 1512. The discharge resistance $R_1$ 1506 can be an order of magnitude (or more) larger than the sensing discharge resistance $R_2$ 1509 (e.g., $R_1$ can be about 10 GΩ and $R_2$ can be about 10 kΩ). The microswitch is configured to close (reversibly) when pressure applied to the sensor equals and/or exceeds a predefined threshold. For example, after the NUC 1503 is charged to an initial voltage Vo, the NUC 1503 experiences a trickle discharge through resistor $R_1$ 1506.

Figure 15B:
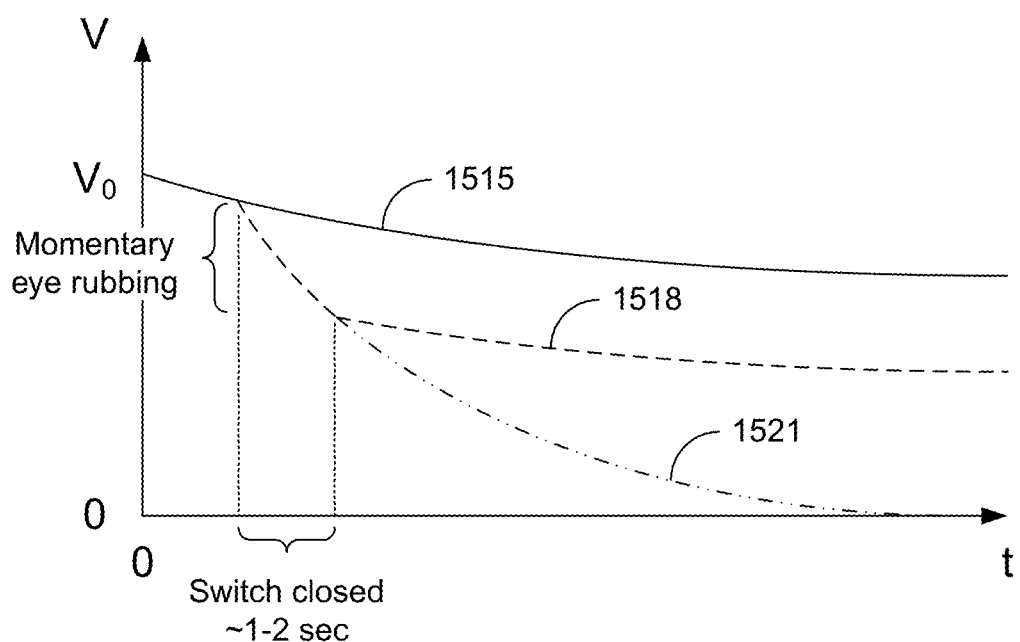

As illustrated in FIG. 15B, the normal trickle discharge follows a slow $e^{-t}$ exponential decay as shown by curve 1515 when the microswitch 1512 is open. When the sensed pressure (e.g., from a glaucoma spike or rubbing of the eye) meets or exceeds the threshold condition, the microswitch 1512 closes (reversibly) and the NUC 1503 discharges at an increased rate because of the reduced resistance of the sensing discharge resistor $R_2$ 1509. As illustrated by curve 1518 of FIG. 15B, the discharge rate increases for as long as the microswitch 1512 is closed. In the case of someone rubbing their eye (e.g., for about 1-2 seconds), the NUC 1503 discharges at the accelerated rate until the pressure is removed, where the microswitch 1512 opens again and the NUC 1503 continues to discharge at the trickle rate limited by the discharge resistance $R_1$ 1506. In the case of a natural glaucoma IOP spike (which can be 1-2 orders of magnitude longer than the artificial spike produced by rubbing the eye), the sensed pressure can continue to exceed the threshold for minutes. Because the increased pressure is maintained for an extended period of time, the NUC 1503 discharges at the accelerated rate until it is discharged (or nearly discharged), as illustrated by curve 1521 of FIG. 15B. The NUCs described herein can be extended for use in other miniaturized implantable sensors and/or devices. In some implementations, the sensor and/or device can include a plurality of NUCs 1503, which may be connected in parallel to store more energy and obtain slower discharge. The NUCs 1503 can be stacked, positioned adjacent to each other, or can be distributed in the same or different planes, respectively.

Device Capacitance, Resistance, and Charge Stored.

NUC devices were built by deposition of metal on one side of porous alumina membranes and subsequent electroplating metal in pores to fill them to about ¾ of their length. Subsequently, in some cases the unfilled portions of pores were filled by dielectric materials. Finally metal was deposited on the other side of the membrane. Capacitances of such fabricated devices were of primary interest and thus were measured. For comparison between NUCs built using different materials and with different geometries we used volumetric capacitance densities (VCD) expressed in F/cm$^3$. For NUCs built using membranes of the same thickness it may be convenient to use the surface capacitance densities (SCD). The capacitance densities of building devices are influenced by many factors such as material of membranes, the membrane thickness, the pores density, metal electroplated, and any dielectric material deposited in pores after electroplating. Experiments in making NUCs with membranes of 50 µm thickness showed SCD in the order of 25 mF/cm$^2$-29 mF/cm$^2$. The thickness of NUCs was in the order of 60 µm. It should be stated that SCD is influenced by materials and geometry of membranes. The volume of the implantable capacitor can be limited to, e.g., 1 mm×2 mm×1 mm. For example, the volume of the implantable capacitor can be equal to or less than 1000 mm$^3$, 100 mm$^3$, 10 mm$^3$, 5 mm$^3$, 3 mm$^3$, 2 mm$^3$, or 1 mm$^3$. Thus, with a volume of 2 mm$^3$ the NUC with a surface area of 1 mm×2 mm would have a capacitance $C_N$=(29 mF/cm$^2$)×2 mm$^2$=0.58 mF. Considering the volume available for the capacitor it may be assumed that this capacitor can be composed of 10 NUCs (each with a surface area 1 mm×2 mm and thickness of 60 µm) connected in parallel. This structure would yield a total capacitance $C_T$=5.8 mF. The equivalent self-discharge of the NUC is $R_{sd}$=900 MΩ. The parallel connection of 10 NUCs will have the effective self-discharge resistance $R_{sd}$=(900/10) MΩ=90 MΩ. When the operating voltage of the capacitor is 3V, the total charge stored is $Q_T$=17.5 mC. By utilizing custom made membranes, the thickness may be reduced and thus the number of NUCs may be increased for the same volume.

Device Self-Discharge.

The loss of charge in the sensor capacitor during the 24 hours stand-by mode can be evaluated using the time constant $T_d$=$R_{sdT}C_T$, which for the above given parameters is $T_d$=$R_{sdT}C_T$=145 hrs. Thus, in a 24 hours stand-by mode, the charge, $Q_T$, decreases exponentially to the level $Q_T e^{-24/145}$=0.998 $Q_T$, i.e., drops by 0.25%.

Device Charge Time.

The charge time is on the order of seconds. It should be noted that the charge time is also dependent on the output impedance of the source that is charging the device. NUCs can be charged, e.g., through inductive coupling via an implanted coil, or through proper external radiation stimulation of an implanted solar cell (or similar reception device).

Device Discharge Time.

The discharge time of the capacitor depends on the equivalent series resistance (ESR) and the impedance of the load. In experiments conducted to date, the load was the switch in the potentiostat, which is on the order of mΩ. The observed discharge down to about 15% of the full charge exhibits a very fast drop (~j msecs). Further studies with specialized instrument and methodology adjusted to the features of NUC can be conducted for a given load. The discharge can depend on the sensor circuit (see, e.g., FIG. 15A) and other components, if any, as well.

The novel technology for building capacitors based on anodization of aluminum sheets of thickness on the order of 1 mm or less (other thicknesses can be used as well) can be used to build sensor capacitors. 60 µm thick custom alumina membranes of 2 types have been fabricated: one with pores of 30 nm diameter and another with 60 nm diameter. These membranes were successfully used to build NUCs. For sensor capacitors, the membranes should be, e.g., approximately 1 mm thick (or less) with pores of 30 nm diameter to yield higher capacitance density. The length of the electroplated wires can be optimized to maximize the capacitance. In the experiments, it was observed that the capacitance increases significantly with the length of the nanowires. The advantages of building sensor capacitors using this novel approach are:

a) Simpler manufacturing, less external interconnections, and easy packaging;
b) Higher self-discharge resistance, in comparison to 10 parallel NUCs; and
c) Higher capacitance density (lower device volume in comparison to 10 parallel NUCs).

Anodization of aluminum forming porous membranes of the typical dimensions: Membrane diameter 1.75 mm-2 mm, membrane thickness: 0.75 mm-1 mm, length of the pores 100 um, pore diameters: 30 nm, 50 nm and 100 nm. The membranes can be used for deposition of conducting materials into the pores. The following types of anodization can be used: anodization to form one-sided membranes, and anodization of two-sided membranes. One-sided membranes comprise pores terminated on one side by the alumina barrier with an additional deposition of dielectric material (if needed) such as an existing nano-amorphous carbon (e.g., from Sigma Technologies Intl, LLC). The additional layer of dielectric material increases the dielectric strength of the structure, and/or allows the device to operate at higher voltages, if needed. Two-sided membranes comprise the upper part of the porous alumina layer separated from the aluminum layer by the natural alumina barrier, and the lower porous alumina layer will be separated from the same layer of aluminum by another natural alumina barrier. The typical thickness of the natural alumina barrier is about 30 nm. The thickness of the natural alumina barrier, the pore diameter and the length of pores are controlled by the anodization conditions: chemistry, voltage and temperature. These conditions can be determined experimentally to obtain the desired parameter values.

Deposition of Conducting Materials in the Pores.

Considered conducting materials include platinum or two special carbon forms such as graphene or carbon nanotubes. Two different techniques for deposition of the conducting materials can be used: electroplating for deposition of platinum, and initial electroplating of nickel as a starter for synthesis of graphene and/or carbon nanotubes in the membranes. The deposition of the selected carbon forms can be developed in cooperation with a third party (e.g., MER Corp., Tucson Ariz.).

Measurement Techniques for Determination of Parameters of Fabricated Devices.

Experience in measuring of similar NUC devices built with the use of commercial membranes indicated that the devices are nonlinear, and thus the measurement techniques have to be very sophisticated and utilize high quality measurement instruments (e.g., such as those provided by Tektronix or Keithley-Tektronix companies, for example Keithly SMU 2450). Model parameters, such as capacitance, equivalent series resistance, and self-discharge resistance, depend on the voltage level, and consequently measurements of those parameters involve device operations with carefully selected time forms of excitation signals (i.e., voltages or currents). Use of impedance measurements was excluded due to the strong nonlinearity of the devices.

Another important feature of the energy storage devices is their lifetime. The lifetime can be very long (much longer than that of batteries) because the operation of the devices (charging and discharging) does not involve any chemical operations. The chemical operations in batteries involve ion transfers that can cause wear of the material. The charge and discharge operations in case of the NUCs for powering implantable sensors and/or devices involve electrostatic changes with only electron transfers, and thus any material wear is negligible.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A device for implantation in a subject, comprising:
   circuitry for sensing presence and duration of an observable parameter of the subject; and
   a power source comprising a nanowired ultra-capacitor (NUC) having a negligible intrinsic self-discharge rate of 2 nA or less and a high self-discharge resistance of 250 MΩ or more, the power source configured to provide electrical power to the circuitry for sensing the observable parameter, where the presence and duration of the observable parameter are based upon sensed changes in discharge rate of the NUC.

2. The device of claim 1, wherein the observable parameter is intraocular pressure (IOP).

3. The device of claim 1, wherein the circuitry comprises a pressure sensitive microswitch.

4. The device of claim 1, wherein the power source has a volume of 10 mm$^3$ or less.

5. The device of claim 1, wherein the volume of the power source is 5 mm$^3$ or less.

6. The device of claim 1, wherein the volume of the power source is 2 mm$^3$ or less.

7. The device of claim 1, wherein the power source comprises a plurality of NUCs coupled in parallel.

8. The device of claim 7, wherein the plurality of NUCs are stacked.

9. The device of claim 7, wherein the plurality of NUCs are adjacent to each other.

10. The device of claim 7, wherein the plurality of NUCs are disjointly distributed in a common plane or in different planes.

11. The device of claim 7, wherein the plurality of NUCs are disjointly distributed in different locations.

12. The device of claim 7, wherein the plurality of NUCs have a total capacitance that is approximately proportional to the number of NUCs.

13. The device of claim 1, wherein the NUC has a surface capacitance density in a range from about 25 mF/cm$^2$ to about 29 mF/cm$^2$ or greater.

14. The device of claim 1, wherein the device is an ocular diagnostic device.

15. The device of claim 1, wherein the circuitry senses intraocular pressure (IOP).

16. The device of claim 1, wherein the subject is a human being.

17. The device of claim 1, wherein the subject is an animal.

18. The device of claim 1, wherein the circuitry for sensing the observable parameter and the power source comprising the NUC are implanted in the subject, the power source electrically coupled to the circuitry for sensing the observable parameter.

19. The device of claim 18, wherein the power source is charged via an implanted solar cell.

20. The device of claim 18, wherein the power source comprises a plurality of NUCs disjointly distributed in a common location or in different locations in the subject.

* * * * *